(12) United States Patent
Brown et al.

(10) Patent No.: US 10,526,395 B2
(45) Date of Patent: Jan. 7, 2020

(54) DETERGENT-PROTEIN COMPOSITION COMPRISING LYOPHILIZED DETERGENT-SOLUBILIZED PROTEIN

(71) Applicant: ARIZONA BOARD OF REGENTS ON BEHALF OF THE UNIVERSITY OF ARIZONA, Tucson, AZ (US)

(72) Inventors: Michael F. Brown, Tucson, AZ (US); Suchithranga Perera, Tucson, AZ (US); Udeep Chawla, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/763,052

(22) PCT Filed: Sep. 30, 2016

(86) PCT No.: PCT/US2016/054954
§ 371 (c)(1),
(2) Date: Mar. 23, 2018

(87) PCT Pub. No.: WO2017/059334
PCT Pub. Date: Apr. 6, 2017

(65) Prior Publication Data
US 2018/0273606 A1 Sep. 27, 2018

Related U.S. Application Data

(60) Provisional application No. 62/263,295, filed on Dec. 4, 2015, provisional application No. 62/235,335, filed on Sep. 30, 2015.

(51) Int. Cl.
*C07K 14/72* (2006.01)

(52) U.S. Cl.
CPC .................. *C07K 14/723* (2013.01)

(58) Field of Classification Search
CPC .................................................. C07K 14/723
See application file for complete search history.

(56) References Cited

U.S. PATENT DOCUMENTS

| 6,172,262 | B1 | 1/2001 | McQuade et al. |
| 6,528,271 | B1 | 3/2003 | Bohn et al. |
| 6,586,205 | B1 | 7/2003 | Glucksmann et al. |
| 2006/0188964 | A1 | 8/2006 | Mancia et al. |
| 2013/0324707 | A1 | 12/2013 | Gellman et al. |

FOREIGN PATENT DOCUMENTS

CN 102558344 A 7/2012

OTHER PUBLICATIONS

Aveldano, "Phospholipid Solubilization during Detergent Extraction of Rhodopsin from Photoreceptor Disk Membranes" vol. 324 Issue 2 (Dec. 20, 1995): pp. 331-343.
Bhowmik et al. Rhodopsin Photoactivation Dynamics Revealed by Quasi-Elastic Neutron Scattering. Biophysical Journal, Apr. 8, 2015, 61a.
Caligur, "Detergent Properties and Applications" Sigma-Aldrich: Biofiles, vol. 3 Issue 3 (Nov. 28, 2011).
Grisshammer, Chapter 36 Purification of Recombinant G-Protein-Coupled Receptors Methods in Enzymology, vol. 463, 2009, pp. 631-645.
Izutzu et al. "Stabilizing Effect of Amphiphilic Excipients on the Freeze-Thawing and Freeze-Drying of Lactate Dehydrogenase" vol. 43 Issue 11 (May 1994): pp. 1102-1107.
McQuade et al. "Rigid Amphiphiles for Membrane Protein Manipulation" Angewandte Chemie, vol. 39 Issue 4 (Feb. 18, 2000): pp. 758-761.
Pan et al. "Conformational Dynamics of a Membrane Transport Protein Probed by H/D Exchange and Covalent Labeling: The Glycerol Facilitator" Journal of Molecular Biology, vol. 416 Issue 3 (Feb. 24, 2012).
Perera et al. "Powdered G-Protein-Coupled Receptors" The Journal of Physical Chemistry Letters, vol. 7 Issue 20 (Oct. 10, 2016): pp. 4230-4235.
Ren et al. High-Level Production, Solubilization and Purification of Synthetic Human GPCR Chemokine Receptors CCR5, CCR3, PLoS ONE, Feb. 18, 2009, vol. 4, Issue 2, e4509.
Rey et al. "Effective Removal of Nonionic Detergents in Protein Mass Spectrometry, HydrogenIDeuterium Exchange, and Proteomics" Journal of Molecular Biology, vol. 82 Issue 12 (May 27, 2010).
Zhang et al. "Dynamics of the beta2-Adrenergic G-Protein Coupled Receptor Revealed Hydrogen-Deuterium Exchange" Analytical Chemistry, vol. 82 Issue 3 (Jan. 8, 2010).

*Primary Examiner* — Robert S Landsman
(74) *Attorney, Agent, or Firm* — Ngyuen Tarbet

(57) ABSTRACT

A method for generating detergent-solubilized G-protein coupled receptors (GPCRs) in powdered form. The powdered GPCRs is storable at temperatures of −20° C. or lower and for durations of 365 days or longer without substantial loss of functionality of the GPCRs after rehydration as compared to a pre-frozen state. The method can maintain minimal detergent to protein ratio in molar concentrations. The method can further generate GPCRs with specific water or deuterium content as required in certain experiments, such as mass spectrometry, NMR spectroscopy, or quasi-elastic neutron scattering (QENS).

7 Claims, 6 Drawing Sheets

DETERGENT-PROTEIN COMPOSITION COMPRISING LYOPHILIZED DETERGENT-SOLUBILIZED PROTEIN

CROSS REFERENCE

This application claims priority to U.S. Provisional Patent Application No. 62/263,295, filed Dec. 4, 2015, and U.S. Provisional Patent Application No. 62/235,335, filed Sep. 30, 2015, the specification(s) of which is/are incorporated herein in their entirety by reference.

GOVERNMENT SUPPORT

This invention was made with government support under Grant No. R01 EY012049, awarded by NIH. The government has certain rights in the invention.

FIELD OF THE INVENTION

The present invention features methods of preserving G-protein coupled receptors (GPCRs).

BACKGROUND OF THE INVENTION

G-protein coupled receptors (GPCRs) constitute a large protein family of receptors that sense molecules outside the cell and activate inside signal transduction pathways and, ultimately, cellular responses. Ligands that bind and activate these receptors include light-sensitive compounds, odors, pheromones, hormones, and neurotransmitters, and vary in size from small molecules to peptides to large proteins. GPCRs are integral to a number of disease processes, and are also the target of approximately 40% of all modern medicinal drugs. Despite their critical importance, current understanding of the structure and function of GPCRs is inadequate because of their low natural abundance. Thus, for structural studies, which require milligram quantities of purified membrane protein, production in heterologous systems is required, but has been extremely difficult to accomplish.

Existing GPCR-stabilizing processes are focused on preserving the GPCR once it has been dissolved in detergents. Other GPCR-stabilizing processes require addition of antagonist/agonists that force the GPCR into a more stable inactive state, or require addition of stabilizing lipid-like substances, which requires site-directed mutagenesis of the GPCR to generate a more stable structure. For instance, GPCRs may be separated and purified from different raw materials using affinity chromatography by means of a general affinity tag, such as a poly-histidine tag, or using a subsequent receptor-specific ligand column. If suitable immobilized ligands are unavailable, size-exclusion chromatography or other techniques may be applied.

As another example, CN102558344A relates to a method for separating and purifying GPCRs. The method is characterized in that the GPCRs are separated and purified from different raw materials by an ultrafiltration technology in a key process. US2006/0188964 provides a method for identifying a reagent in which a membrane protein is likely to crystallize, and a method for producing crystals of a protein which, in a cell, is a membrane-bound protein. U.S. Pat. No. 6,528,271 discloses a method of screening a compound for activity in controlling pain. The method comprises determining whether or not the compound inhibits β-arrestin binding to phosphorylated μ-opioid receptor.

The present invention features methods of stabilizing detergent solubilized GPCRs in powdered form, which can be stored at a temperature of −20° C. or lower and for a duration of 365 days or longer without substantial loss of photochemical functionality of the GPCRs after rehydration as compared to their pre-frozen state. None of the above references teaches a dry powdered form of GPCRs as the final product as disclosed in the presently claimed invention.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

SUMMARY OF THE INVENTION

It is an objective of the present invention to provide for methods of preserving G-protein-coupled receptors (GPCRs) that can be later rehydrated without altering their function, as specified in the independent claims. Embodiments of the invention are given in the dependent claims. Embodiments of the present invention can be freely combined with each other if they are not mutually exclusive.

GPCRs are amphiphilic protein that are typically insoluble in buffer solutions due to their non-polar nature, and would require a detergent environment to become solubilized. It was hypothesized that in a detergent environment, the protein would denature if an attempt was made to remove water from the detergent-solubilized GPCRs since the polar region of these amphiphilic proteins require water molecules for stabilization through solvation. However, the inventors have surprisingly discovered a method for preserving the detergent-solubilized GPCRs in a powdered form that is substantially devoid of water (at least 99%) and can be stored at a temperature of −20 C or lower and for a duration of 365 days or longer without substantial loss of photochemical functionality of the GPCRs after rehydration compared to its pre-frozen state. The method described here maintains a minimal detergent to protein ratio in molar concentration and does not require them to remain in liquid solutions. In addition, this method allows hydrogen atoms within the GPCRs to be replaced with deuterons, which is a necessary step to conduct certain experiments.

In one embodiment, the present invention features a method of stabilizing and preserving an amphiphilic protein. The method may comprise providing an amphiphilic protein, providing a detergent solvent comprising a detergent, adding the amphiphilic protein to the detergent solvent, wherein a hydrophobic component of the detergent interacts with a hydrophobic component of the amphiphilic protein, and wherein a hydrophilic component of the detergent interacts with a hydrophilic component of the amphiphilic protein, thereby forming a detergent-solubilized protein, separating the detergent-solubilized protein from the remaining detergent solvent to form a detergent-solubilized protein concentrate, and lyophilizing the detergent-solubilized protein concentrate to form a detergent-protein powder.

One of the unique and inventive technical features of the present invention is method of forming the detergent-protein powder. Without wishing to limit the invention to any theory or mechanism, it is believed that the technical feature of the present invention advantageously provides for GPCRs that can be stored for long periods of time with no loss of function. Certain experimental procedures require GPCRs in milligram quantities. The method described herein may allow for large-scale production of GPCRs for drug-discovery purposes since the GPCRs can be stabilized for long periods of time and reconstituted as needed. Additionally, the process can generate GPCRs with specific water or deuterium content as required in certain experiments, such as mass spectrometry, NMR spectroscopy, or quasi-elastic neutron scattering. None of the presently known prior references or work has the unique inventive technical feature of the present invention.

BRIEF DESCRIPTION OF THE DRAWINGS

The features and advantages of the present invention will become apparent from a consideration of the following detailed description presented in connection with the accompanying drawings in which.

DESCRIPTION OF PREFERRED EMBODIMENTS

As used herein, an "amphiphilic protein" is defined as a protein having polar or water-soluble groups attached to nonpolar or water-insoluble groups. A non-limiting example of an amphiphilic protein is a G-protein coupled receptor (GPCR), such as Rhodopsin, a class A GPCR responsible for vision under dim-light conditions in vertebrates. As used herein, the term "G-protein" is be defined as a guanine nucleotide-binding protein that can act as a molecular switch inside cells, and is involved in transmitting signals from a variety of stimuli outside a cell to its interior. In exemplary embodiments, the GPCR may be extracted from bovine retina.

As used herein, the term "detergent" is defined as a compound having both hydrophilic and hydrophobic (or lipophilic) groups. A non-limiting example of the detergent is 3-[(3 Cholamidopropyl) dimethylammonio]-1 propanesulfonate) (CHAPS) detergent. According to some embodiments, the detergent environment may comprise a buffer solution and a nonionic, an anionic, a cationic or a zwitterionic detergent for solubilizing the protein. As used herein, the term "zwitterionic" is defined as simultaneously having both ionic states (cationic and anionic) in the same molecule.

The detergent environment may further comprise a metal salt. In some embodiments, the buffer solution is a phosphate buffer solution. However, any suitable buffer solution may be used when practicing the invention.

As used herein, the term "lyophilizing" of "freeze-drying" is defined as the process of isolating a solid substance from solution by freezing the solution and evaporating the ice under vacuum.

As used herein, the term "substantially free" refers to being greater than about 90% free of a substance. In some embodiments, "substantially free" can refer to being greater than about 95%, or greater than about 96%, or greater than about 97%, or greater than about 98%, or greater than about 98% free of a substance.

Referring now to FIG. 1-6, the present invention features a method of stabilizing and preserving an amphiphilic protein. In one embodiment, the method may comprise providing an amphiphilic protein, providing a detergent solvent comprising a detergent, adding the amphiphilic protein to the detergent solvent, wherein a hydrophobic component of the detergent interacts with a hydrophobic component of the amphiphilic protein, and wherein a hydrophilic component of the detergent interacts with a hydrophilic component of the amphiphilic protein, thereby forming a detergent-solubilized protein, separating the detergent-solubilized protein from the remaining detergent solvent to form a detergent-solubilized protein concentrate, and lyophilizing the detergent-solubilized protein concentrate to form a detergent-protein powder.

Figure 4:
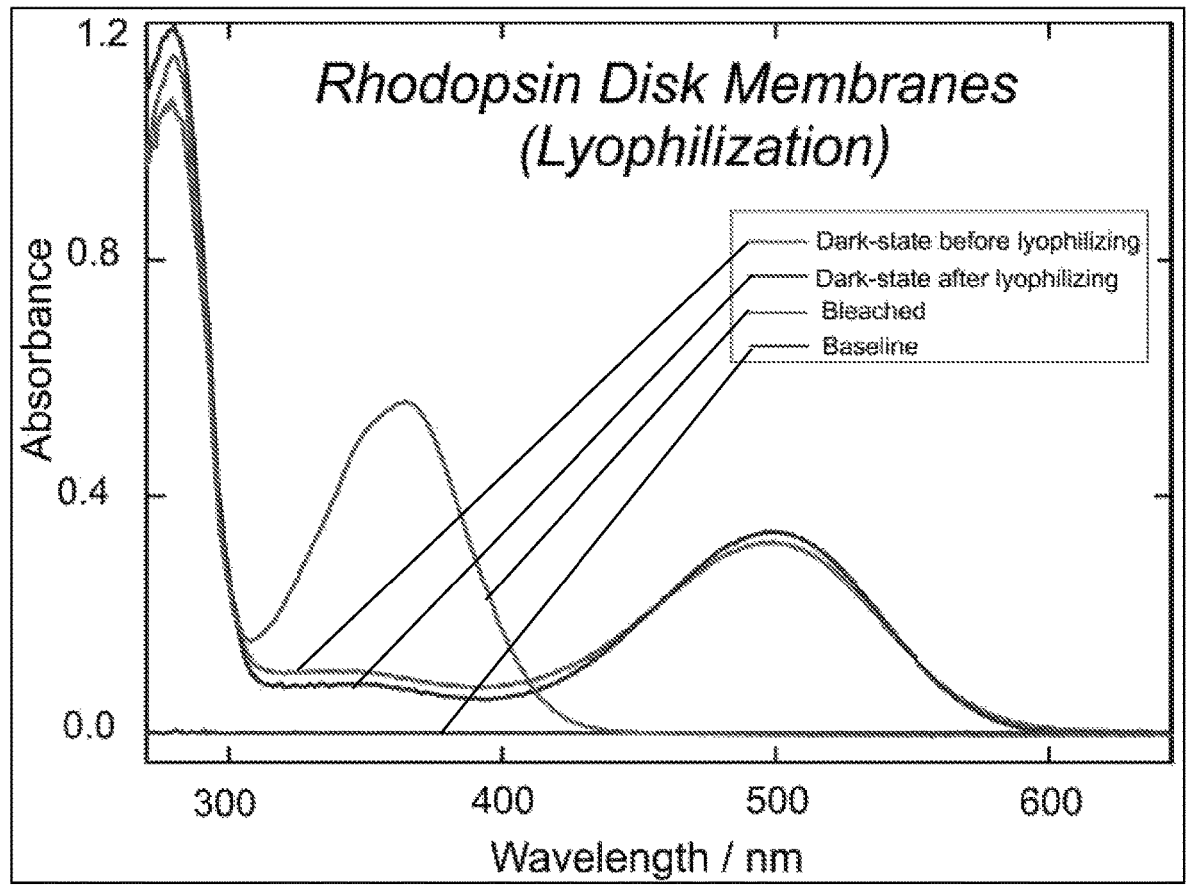
FIG. 4 shows characterization of the rehydrated rhodopsin disk membrane powder prepared from bovine retinas. Dark-state rhodopsin absorbs strongly at 500 nm. After complete photobleaching in the presence of hydroxylamine, the purity (A280/A500) of the rhodopsin in disk membranes solubilized in ammonyx LO detergent was determined to be 2.4.
Figure 5:
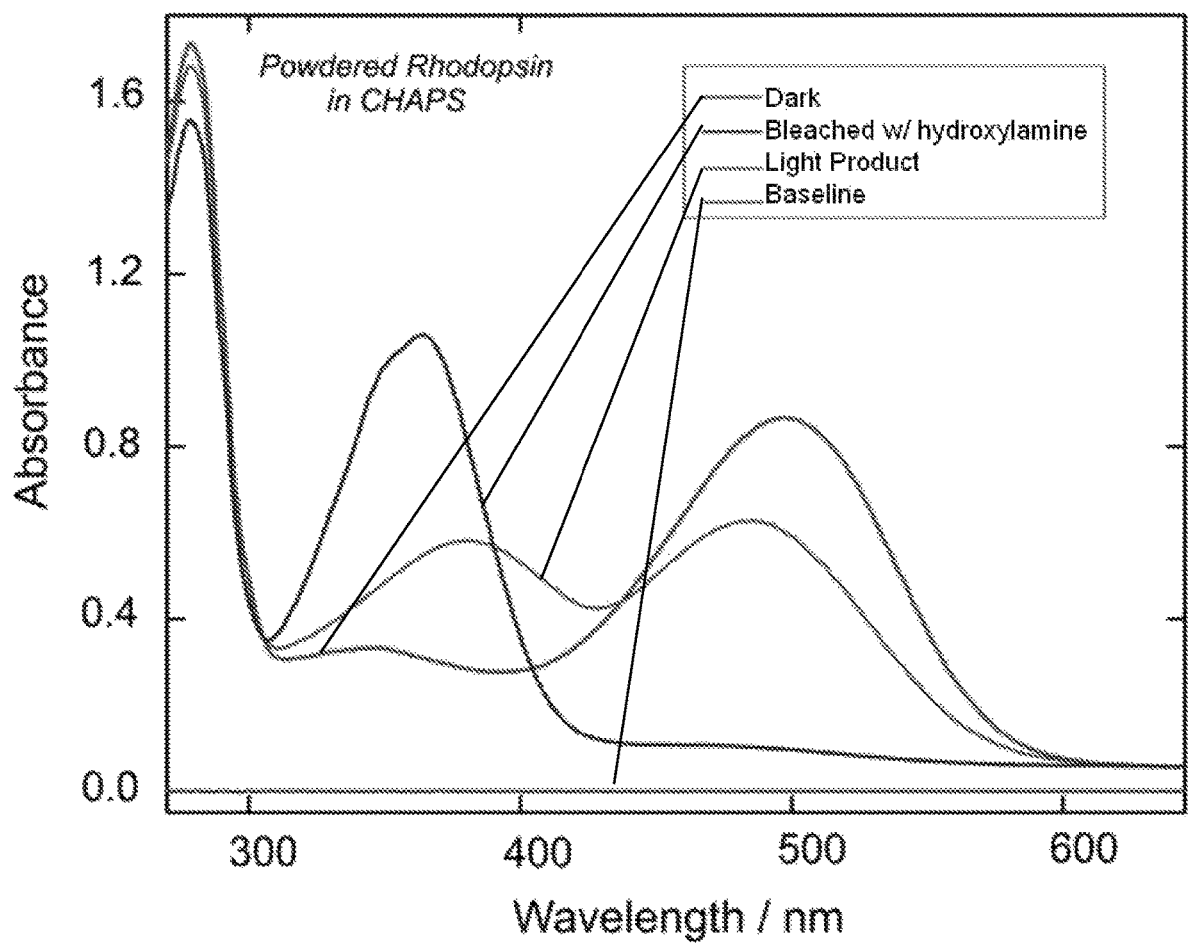
FIG. 5 shows UV-visible spectra for rhodopsin-CHAPS complex after lyophilization for dark state, light activated state, and when bleached with opsin. The powdered rhodopsin-CHAPS detergent complex retains its photochemical functionality upon rehydration.
Figure 6:
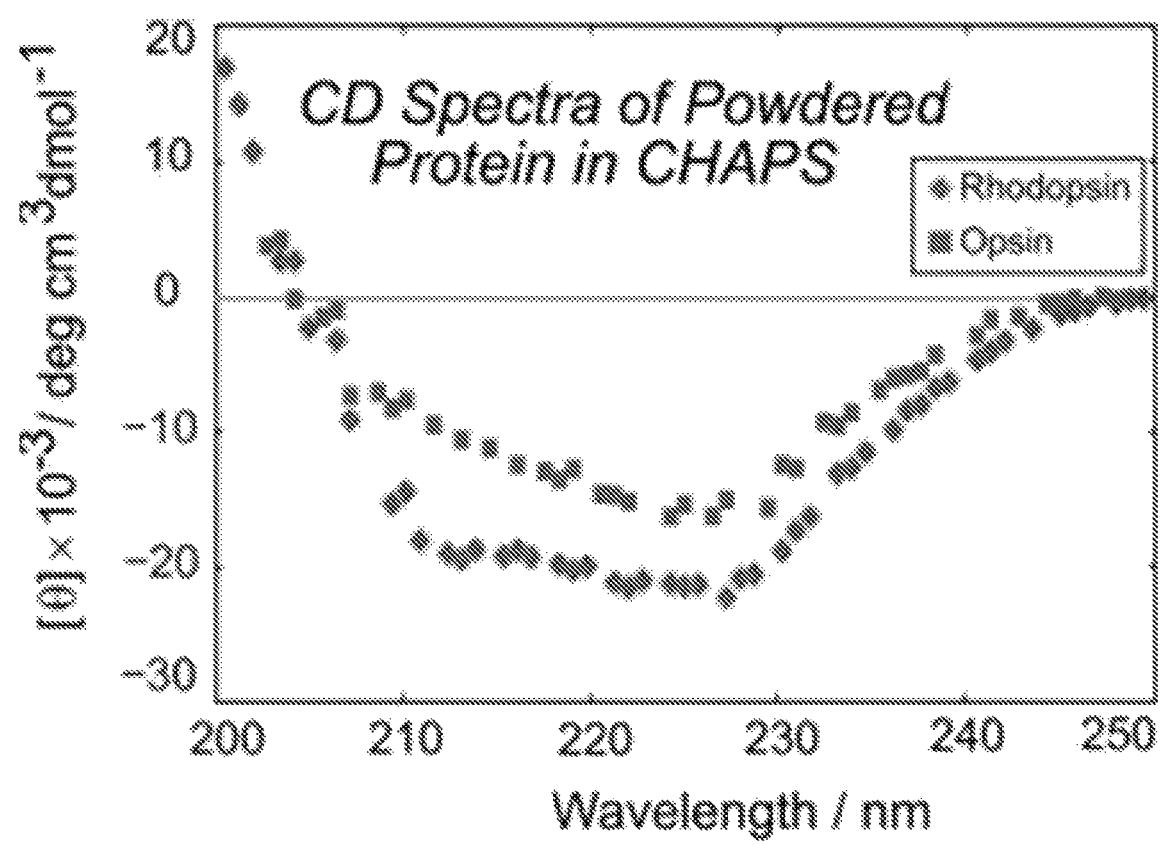
FIG. 6 shows circular dichroism (CD) spectra for re-solubilized powdered rhodopsin and powdered opsin. The powdered rhodopsin-CHAPS detergent complex retains its native helicity upon rehydration.

Conventional practices follow that in a detergent environment, a protein would denature if an attempt was made to remove water since the polar region of these amphiphilic proteins require water molecules for stabilization. However, the method of the present invention can surprisingly stabilize and preserve amphiphilic protein in the detergent-protein powder without denaturizing the protein. Without wishing to limit the present invention to a particular theory or mechanism, the method can enable the preservation of the amphiphilic protein such that when the detergent-protein powder is rehydrated after being stored, the amphiphilic protein regains its photochemical functionality and maintains its structure as compared to its unpreserved state, as shown in FIG. 4-6.

In some embodiments, the detergent-protein powder may be stored at a temperature of at most about −20° C. In some embodiments, the detergent-protein powder may be stored for a duration of at least 365 days.

Figure 3:
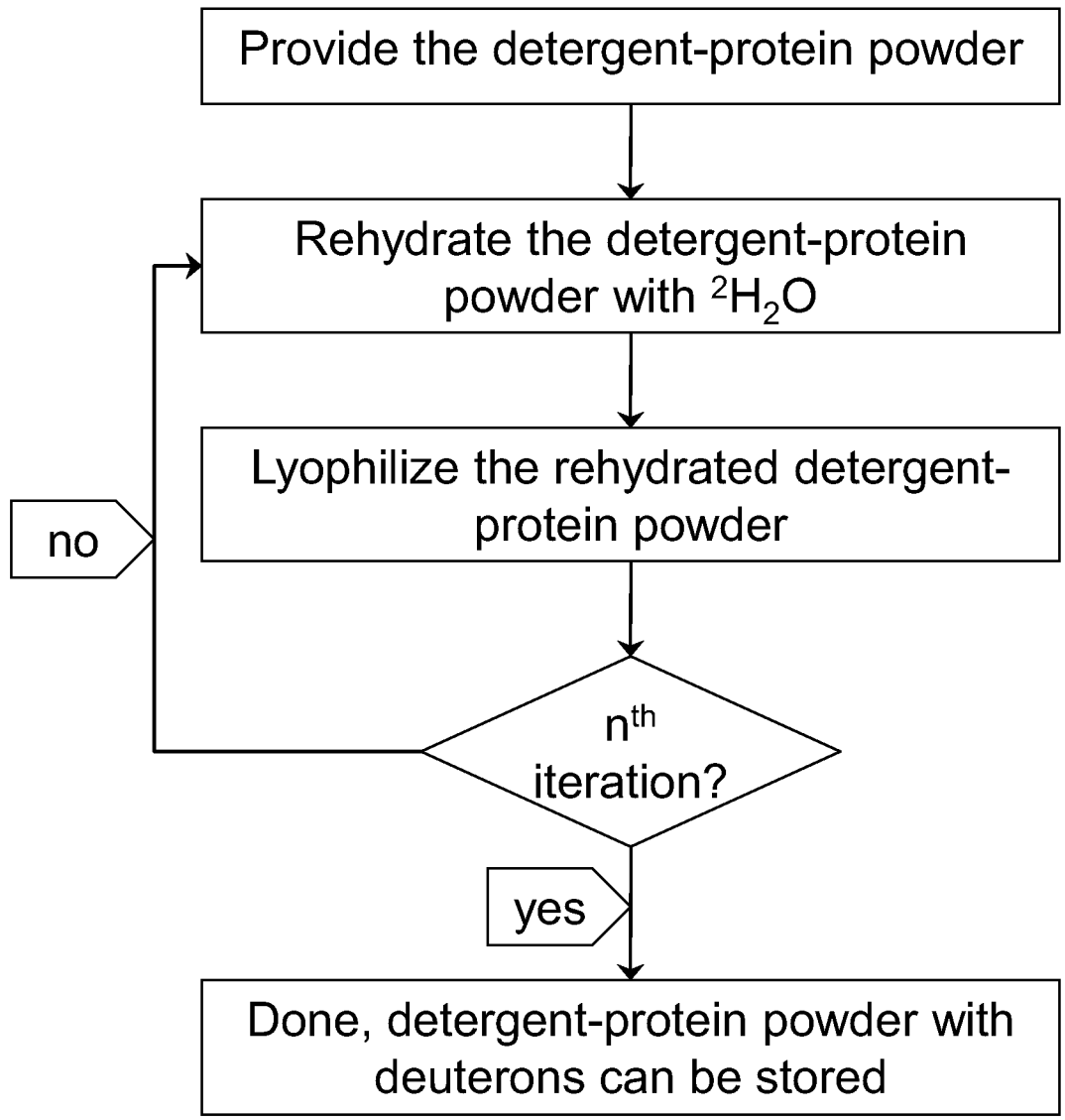
FIG. 3 shows a non-limiting example of replacing exchangeable protons of the detergent-protein powder with deuterons.

According to another embodiment, the method may further comprise replacing exchangeable protons of the detergent-protein powder with deuterons, as shown in FIG. 3. As known to one of ordinary skill in the art, deuterons are isotopes of hydrogen composed of a proton and a neutron. The step of replacing exchangeable protons with deuterons may comprise rehydrating the detergent-protein powder with $^2H_2O$, lyophilizing the rehydrated detergent-protein powder, and repeating the rehydration and lyophilization for a number of iterations, thereby substituting the exchangeable protons with deuterons. In some embodiments, the number of iterations can range from about 2-5 to ensure that all the exchangeable protons are substituted with deuterons. For example, the rehydration and lyophilization may be repeated up to three times.

In one embodiment, the amphiphilic protein is a G-protein coupled receptor (GPCR). Preferably, the amphiphilic protein is substantially free of water. For instance, the amphiphilic protein may be 99% free of water.

In some embodiments, the step of providing the amphiphilic protein may comprise extracting the amphiphilic protein from a protein source. In an exemplary embodiment, the amphiphilic protein is rhodopsin extracted from bovine retina. An example thereof is later described in Example 1.

According to one embodiment, the detergent can be a nonionic, an anionic, a cationic or a zwitterionic detergent. A non-limiting example of the detergent is 3-[(3-cholamidopropyl)-dimethylammonio]-1-propanesulfonate (CHAPS), which is a zwitterionic detergent.

According to another embodiment, the detergent solvent may further comprise a buffer solution and a metal salt. In one embodiment, the metal salt is zinc acetate. An example of the buffer solution is a phosphate buffer, such as a sodium phosphate buffer. However, it is understood that other buffers may be used in the present invention.

In one embodiment, the detergent-solubilized protein is separated from the remaining detergent solvent by centrifugation. In centrifugation, the supernatant is removed or decanted, thereby leaving the detergent-solubilized protein concentrate.

Figure 1:
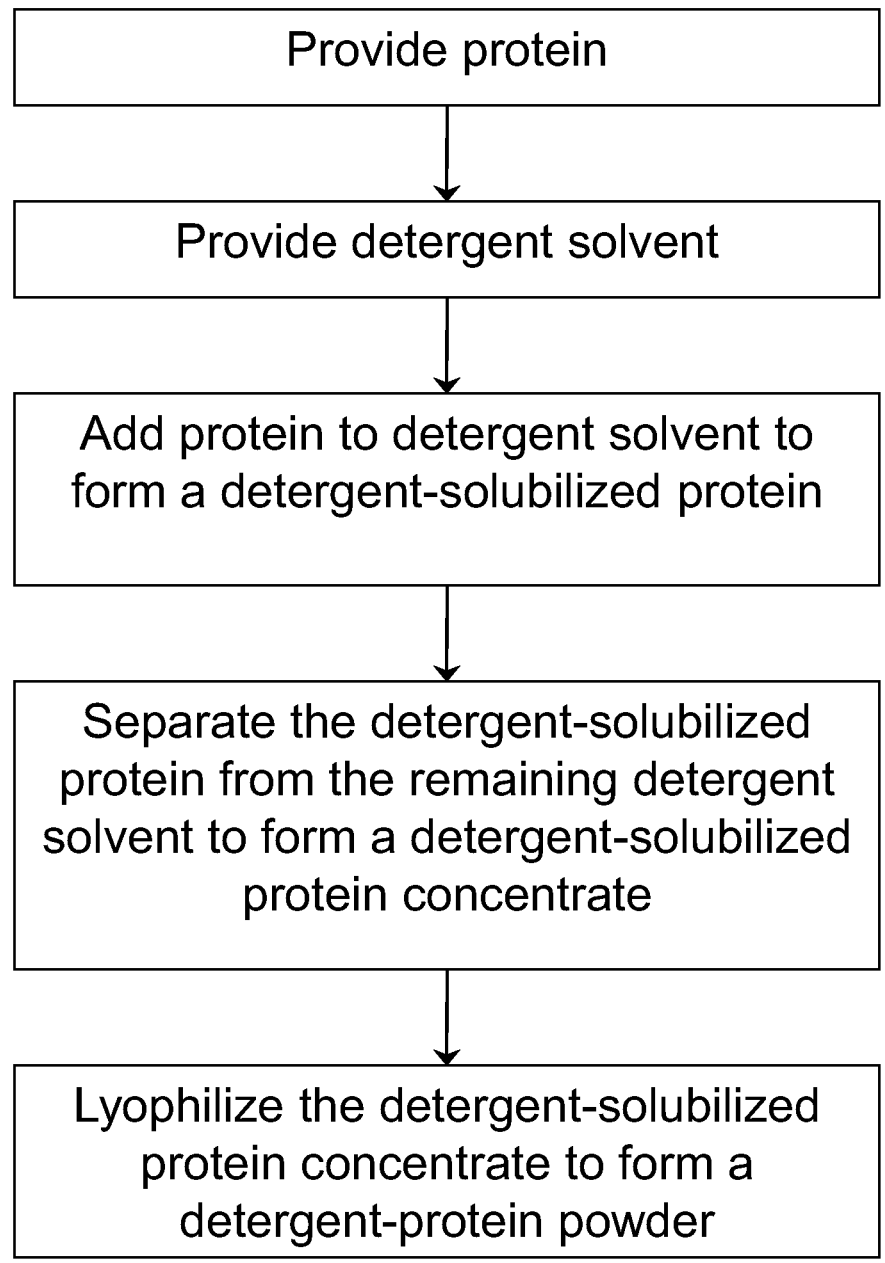
FIG. 1 shows a non-limiting example for preserving amphiphilic proteins according to an embodiment of the present invention.
Figure 2:
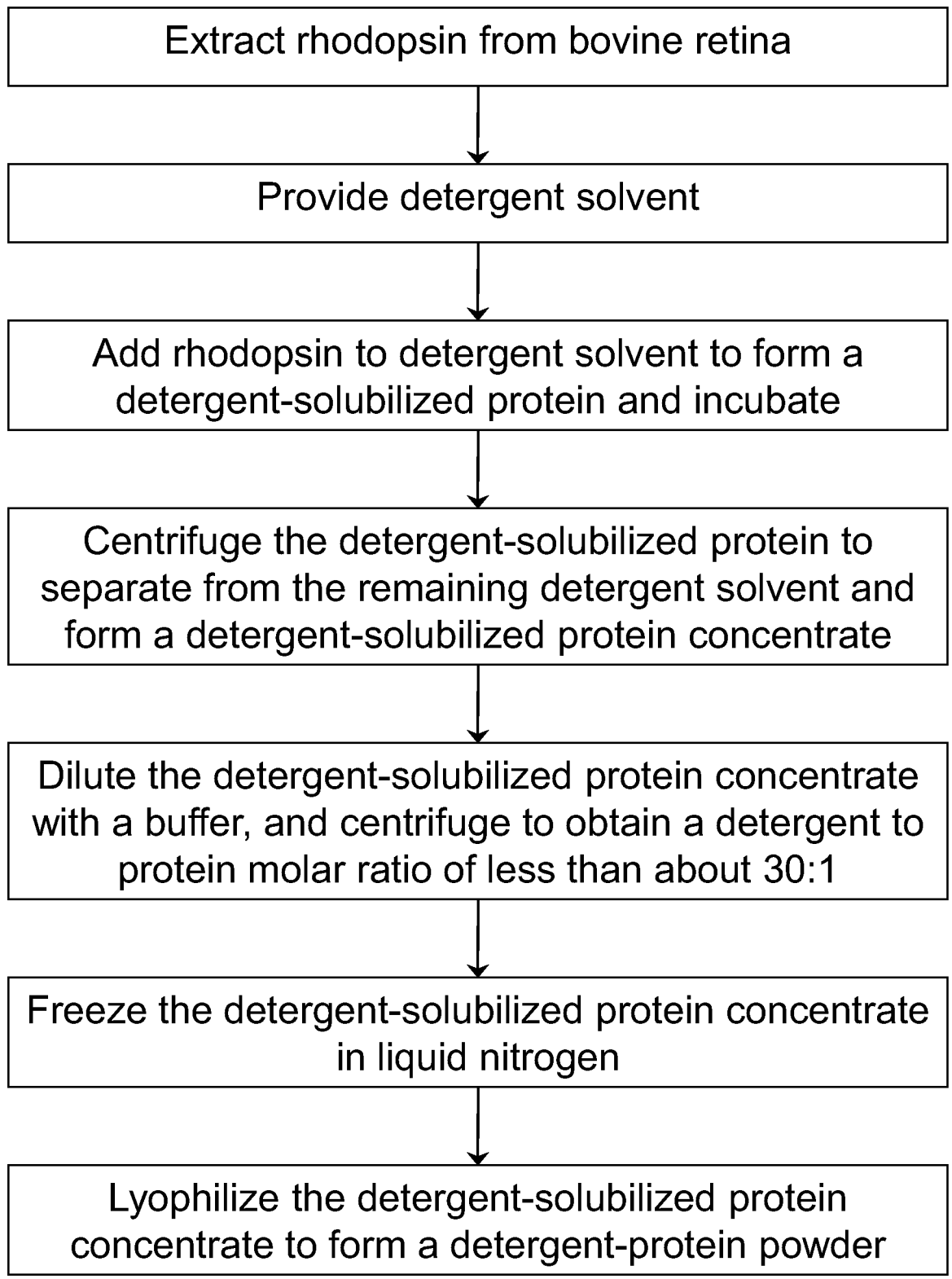
FIG. 2 shows an alternative embodiment for preserving the amphiphilic proteins.

In some embodiments, as shown in FIG. 2, the method may further comprise diluting the detergent-solubilized protein concentrate with a buffer, and centrifuging to obtain a detergent to protein molar ratio of less than about 30:1, prior to lyophilizing. For example, the phosphate buffer may be used for further dilution. In other embodiments, the detergent to protein molar ratio can range from about 25:1 to 29:1. In further embodiments, the detergent to protein molar ratio is about 29:1, about 28:1, about 27:1, about 26:1, or about 25:1.

In still further embodiments, as shown in FIG. 2, the method may comprise freezing the detergent-solubilized protein concentrate in liquid nitrogen prior to lyophilizing.

According to another embodiment, the present invention features a lyophilized, detergent-protein composition comprising an amphiphilic protein and a detergent, with a molar ratio of the detergent to amphiphilic protein is at most about 30:1. It is theorized that a hydrophobic component of the detergent interacts with a hydrophobic component of the amphiphilic protein, and a hydrophilic component of the detergent interacts with a hydrophilic component of the amphiphilic protein, thereby resulting in the detergent-protein composition. In a preferred embodiment, the composition is in a powdered form.

Without wishing to limit the present invention to any theory or mechanism, the lyophilized, detergent-protein composition is capable of being stored at a temperature of at most about −20° C. and for a duration of at least about 365 days. Further still, when the detergent-protein powder is rehydrated after being stored, the amphiphilic protein regains its photochemical functionality and maintains its structure as compared to its unpreserved state.

In one embodiment, the exchangeable protons of the detergent-protein composition are substituted with deuterons.

In some embodiments, the amphiphilic protein is substantially free of water. For example, the amphiphilic protein may be at least about 90% free of water, or at least about 95% free of water, or at least about 99% free of water.

According to one embodiment, the amphiphilic protein may be a G-protein-coupled receptor (GPCR). For instance, the amphiphilic protein is rhodopsin extracted from bovine retina. According to another embodiment, the detergent is a nonionic, an anionic, a cationic or a zwitterionic detergent, such as 3-[(3-cholamidopropyl) dimethylammonio]-1-propanesulfonate (CHAPS). In some embodiments, the detergent to amphiphilic protein molar ratio ranges from 25:1 to 29:1. In other embodiments, the detergent to amphiphilic protein molar ratio is about 29:1, about 28:1, about 27:1, about 26:1, or about 25:1.

EXAMPLES

The examples described herein are for illustrative purposes only and are not intended in any way to limit the present invention to said examples. Equivalents or substitutes are within the scope of the present invention.

Example 1: Preparation of Rhodopsin Disk Membranes

All procedures were carried out under dim red-light (11-W Bright Lab™ Universal Red Safelight bulb, CPM Delta1, Inc.), at 4° C. Rhodopsin disk membranes (RDM) were isolated from bovine retinas. The RDM pellet was re-suspended in 15 mM sodium phosphate buffer, pH 6.9, and characterized using UV-visible spectroscopy to determine the purity (A280/A500 absorption ratio was typically 2.4). The rhodopsin concentration was estimated using the absorbance of the sample at 500 nm. The difference in absorbance at 500 nm between the dark state and the photo-bleached state (in the presence of hydroxylamine) was used (A500, Dark-A500, Bleached). Note that the 1 OD at 500 nm is equivalent to 1 mL of 1 mg/mL rhodopsin. The sample was photo-bleached with green LED light of 515 nm, which activates rhodopsin to form meta-rhodopsin-II (MII). Including hydroxylamine ensures complete photo-bleaching of the dark-state rhodopsin, and is confirmed by the nearly zero absorbance at ~500 nm.

Example 2: Purification of Rhodopsin in CHAPS Detergent

The RDM (final rhodopsin concentration of 400 µM) was dissolved in 15 mM sodium phosphate buffer, pH 6.9 containing 100 mM CHAPS, and 100 mM zinc acetate, and incubated for 30 min at 4° C. The hydrophobic part of the detergent interacts with the hydrophobic part of the protein, while the hydrophilic part interacts with the polar solvent, making the membrane protein soluble in water. It was centrifuged at 24,000×g (Sorvall SS-34 rotor) for 30 min. This solution was diluted with two volumes of sodium phosphate buffer, pH 6.9 and centrifuged at 24,000×g (Sorvall SS-34 rotor) for 30 min. The resultant supernatant was characterized using UV-visible spectroscopy to determine the quantity and purity. The CHAPS-solubilized rhodopsin was diluted with 15 mM sodium phosphate buffer, pH 6.9, to adjust the detergent to rhodopsin ratio to be 25:1. A total of about 2000 mg of rhodopsin in RDM was solubilized to prepare the powdered dark-state and opsin samples.

Example 3A: Preparation of Powdered Rhodopsin

The rhodopsin-CHAPS complex concentration was increased up to 30 mg/mL (diluted before characterization with UV-visible spectroscopy). Note that the CHAPS micelles have a molecular weight of about 6 kDa, which is about 5 times less than the molecular weight cut-off (30 kDa) of the ultracentrifugal filters. Therefore, it was assumed that during centrifugation, the concentration of the CHAPS detergent concentration remains the same, while the rhodopsin-detergent complex concentration increases. Next, the rhodopsin-CHAPS samples were frozen using liquid nitrogen, and lyophilized under 100-mTorr vacuum for 12 hrs. The resulted powder was rehydrated with 99% $^2H_2O$ (Sigma-Aldrich, St. Louis, Mo.), and lyophilized again for 12 hrs. This latter step was repeated 3 times to ensure complete substitution of the exchangeable protons with deuterons. A part of the lyophilized rhodopsin-CHAPS sample was rehydrated with distilled water, and characterized using UV-visible spectroscopy. The final A280/A500 ratio was 1.6-1.7 and a total of about 600 mg of powdered rhodopsin were produced. In addition to UV-visible spectrophotometry, dynamic light scattering IDLS) may be used to characterize the results.

Example 3B: Preparation of Powdered Opsin

To prepare the powdered opsin sample, 1% (w/v) hydroxylamine was added to about 400 mg (rhodopsin alone) of the rhodopsin-CHAPS sample, and completely photobleached using a 515-nm LED lamp, before starting the lyophilization step. The presence of hydroxylamine ensures the hydrolysis of the Schiff base linkage between retinal and Lys$^{296}$ upon photoillumination. This hydrolysis of the retinal from the rhodopsin yields the apoprotein, opsin. The opsin sample was lyophilized under 100-mTorr vacuum for 12 hrs. Next, the opsin sample was rehydrated with $^2H_2O$, and lyophilized to remove any remaining $H_2O$. This process was repeated two more times after rehydrating with 99% $^2H_2O$.

Example 4: Sample Preparation for Neutron Scattering Experiments

Rhodopsin was extracted and purified from bovine rhodopsin disk membranes (RDMs) as described above. A powdered membrane protein sample containing 72% (w/w) of photochemically functional bovine rhodopsin and 28% (w/w) of CHAPS (3-[(3Cholamidopropyl) dimethylammonio]-1 propanesulfonate)) detergent was prepared. About 600 mg of the powdered rhodopsin sample was divided into two separate containers, one for preparing a dark-state rhodopsin sample, and other for the ligand-free apoprotein opsin sample. The opsin was prepared by photobleaching the dark-state sample with a locally constructed 515-nm LED light source. Both dark-state rhodopsin and opsin samples were then lyophilized at 100-mTorr vacuum for 12 hrs, and then dissolved in 99.9% $^2H_2O$ (Sigma Aldrich, St. Louis, Mo.), and lyophilized again for 12 hrs. These steps were repeated three times to ensure the complete removal of protiated water from the powdered sample. A portion of the prepared samples was re-dissolved in double-distilled deionized water, and characterized using UV-visible spectroscopy to confirm the photochemical functionality of the protein. The circular dichroism (CD) spectra collected for dark-state rhodopsin and opsin samples confirmed that the helicity is conserved in both the powdered rhodopsin and the powdered opsin samples during the lyophilization. Hence, the present inventions has surprisingly discovered that membrane proteins such as rhodopsin can be prepared as dry powders with either lipids or detergents by removing water without adversely affecting their structures. Thereafter, each of the samples was hydrated with $^2H_2O$ inside a glove box with a hydration level of h~0.28 (i.e., 0.28 gram $^2H_2O$/gram of protein), and enclosed in aluminum foil to prevent exposure to light. The dry protein powders regain their photochemical functionality upon rehydration. Finally, each of the samples was inserted in rectangular aluminum sample holder available at near-backscattering spectrometer (BASIS) for neutron scattering experiments.

Advantages of the present inventions include the preservation of GPCRs that allow for long-term storage and shipping. GPCRs processed in the manner described herein can retain function for one year following flash-freezing, thereby making it feasible to generate a large volume of GPCRs with greater efficiency. Increased GPCR stability relative to other processing methods can allow for centralized manufacture and shipping, thereby allowing for the bypassing of lengthy cloning and purification processes involved in generating GPCRs. The powdered GPCRs can then be thawed as needed with no loss of protein function. Further still, the powdered GPCRs can be rehydrated to a specific concentration, which is useful for experiments that require GPCRs of specific hydration levels, such as quasi-elastic neutron scattering. Replacement of hydrogen with deuterons in the powdered GPCRs can also prove useful in said experiments.

Unlike other GPCR-stabilizing processes that are more concerned with how to preserve the GPCR once it has been dissolved in detergents, the method described herein requires minimal detergents and does not require them to remain in liquid solutions. Further still, the method of the present invention does not require the addition of antagonist/agonists (added to force the GPCR into a more stable inactive state) or the addition of any stabilizing lipid-like substances, nor does it require mutating the GPCR to generate a more stable structure. This simplicity may yield stable, unmodified GPCRs more cheaply than other methods.

The powdered GPCRs can have multiple applications, including, but not limited to, the treatment of exocrine and endocrine mediated disorders such as disorders of airway electrolyte metabolism, i.e. cystic fibrosis, chronic airway infections, and other lung disorders. Further examples are described in U.S. Pat. No. 6,586,205, which is incorporated herein by reference. In combination with phospholipids, these powdered GPCRs can be formed and used as nanodiscs or bicelles. In alternative embodiments, the method of preserving the proteins may also be applied to biomedically important ion channels, such as cystic fibrosis transmembrane conductance regulators (CFTRs).

In some embodiments, the powdered GPCRs may be delivered in the form of an aerosol spray from pressurized container or dispenser that contains a suitable propellant, e.g., a gas such as carbon dioxide, or a nebulizer for delivery to the lung. In other embodiments, the powdered GPCR may be infused into the lung of a mammal by inhalation as an aerosol or may be administered by a transdermal route. In still further embodiments, the powdered GPCRs may also be incorporated above and below the critical micelle concentration (cmc) into membrane bilayers composed of various types of lipids as mimics of cellular membranes.

As used herein, the term "about" refers to plus or minus 10% of the referenced number.

The disclosures of the following patents and applications are incorporated in their entirety by reference herein: CN102558344A, US2006/0188964, U.S. Pat. Nos. 6,586,205 and 6,528,271.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A detergent-protein composition comprising a lyophilized detergent-solubilized protein, said detergent-solubilized protein comprising an amphiphilic membrane protein and a detergent, wherein a molar ratio of the detergent to amphiphilic protein is at most about 30:1, wherein the amphiphilic membrane protein is not irreversibly denatured.

2. The composition of claim 1, wherein the amphiphilic protein is a G-protein-coupled receptor (GPCR).

3. The composition of claim 1, wherein the detergent is a nonionic, an anionic, a cationic or a zwitterionic detergent.

4. The composition of claim 1, wherein the detergent-protein composition is rehydrated from a lyophilized state, wherein the amphiphilic protein regains its photochemical functionality and maintains its structure as compared to its unpreserved state.

5. The composition of claim 1, wherein the functionality and structure of the amphiphilic protein is maintained in the lyophilized state.

6. The composition of claim 5, wherein the composition is in a powdered form, wherein the powdered composition is capable of being stored at a temperature of at most about $-20°$ C. and for a duration of at least about 365 days, wherein the powdered composition is capable of being rehydrated after being stored, wherein when the powdered composition is rehydrated, the amphiphilic protein regains its photochemical functionality and maintains its structure as compared to its unpreserved state.

7. A detergent-protein composition comprising a lyophilized detergent-solubilized protein, said detergent-solubilized protein comprising an amphiphilic membrane protein and a detergent, wherein the amphiphilic membrane protein is not irreversibly denatured.

* * * * *